(12) United States Patent
Chen et al.

(10) Patent No.: US 7,578,614 B2
(45) Date of Patent: Aug. 25, 2009

(54) THERMAL RESISTANCE MEASURING APPARATUS

(75) Inventors: Xiao-Zhu Chen, Shenzhen (CN); Zhen-Xing Ye, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 238 days.

(21) Appl. No.: 11/625,288

(22) Filed: Jan. 20, 2007

(65) Prior Publication Data

US 2008/0130705 A1    Jun. 5, 2008

(30) Foreign Application Priority Data

Dec. 1, 2006    (CN) .................... 2006 1 1457317

(51) Int. Cl.
*G01N 25/18* (2006.01)
*H05K 7/20* (2006.01)

(52) U.S. Cl. .................... 374/44; 374/29; 374/137; 374/141; 361/679.52; 361/679.54; 361/688; 361/704

(58) Field of Classification Search .............. 374/4, 374/5, 29, 43–45, 57, 135, 137, 163, 183, 374/185, 208; 702/130–136; 361/679.52, 361/679.54, 688, 704, 157, 158
See application file for complete search history.

(56) References Cited

U.S. PATENT DOCUMENTS

| | | | | |
|---|---|---|---|---|
| 4,696,578 A | * | 9/1987 | Mansuria et al. | 374/45 |
| 5,721,455 A | | 2/1998 | Takashita | |
| 6,157,897 A | * | 12/2000 | Yoshikawa | 702/132 |
| 6,438,504 B2 | * | 8/2002 | Mikubo et al. | 702/132 |
| 6,491,426 B1 | * | 12/2002 | Schonath et al. | 374/45 |
| 7,081,811 B2 | * | 7/2006 | Johnston et al. | 340/449 |
| 2006/0145335 A1 | * | 7/2006 | Teshima et al. | 257/718 |
| 2007/0027981 A1 | * | 2/2007 | Coglitore et al. | 709/224 |
| 2008/0004191 A1 | * | 1/2008 | Ishigaki | 508/155 |
| 2008/0038535 A1 | * | 2/2008 | Fukushima | 428/312.6 |
| 2008/0100826 A1 | * | 5/2008 | Sharpe | 356/51 |
| 2008/0165824 A1 | * | 7/2008 | Ye et al. | 374/43 |
| 2008/0304540 A1 | * | 12/2008 | Danley | 374/11 |

FOREIGN PATENT DOCUMENTS

JP            2004319595 A    *    11/2004

* cited by examiner

*Primary Examiner*—Gail Verbitsky
(74) *Attorney, Agent, or Firm*—Wei Te Chung

(57) ABSTRACT

A thermal resistance measuring apparatus for a heat sink includes a heat source, a temperature sensor, a micro control unit (MCU), a display, and a power apparatus. The heat source heats the heat sink. The temperature sensor senses temperature signals of the heat source. The MCU receives the temperature signals from the temperature sensor and processes them to calculate thermal resistance of the heat sink. The display is electrically connected to the MCU for showing the thermal resistance of the heat sink. The power apparatus supplies power to the heat source, the temperature sensor, and the MCU.

14 Claims, 3 Drawing Sheets

THERMAL RESISTANCE MEASURING APPARATUS

BACKGROUND OF THE INVENTION

1. Field of the Invention

The present invention relates to measuring apparatuses, and particularly to a measuring apparatus that can measure thermal resistances of heat sinks.

2. Description of Related Art

With the increase in heat emission from microelectronic devices and the reduction in overall form factors, thermal management becomes a more and more important element of electronic product design. Heat sinks are used to dissipate heat from a hot surface, usually an enclosure of a heat generating component and thermal resistance is an important factor for determining heat dissipating performance of a heat sink. Thermal resistance data is usually supplied by heat sink manufactures.

However, measuring conditions adapted by the manufacturers are often different from measuring conditions adapted by the designers. Therefore, thermal resistance data supplied by the manufacturers are not useful for designers to design an optimal heat dissipation configuration for a computer system. Oftentimes, designers must retest the thermal resistances of heat sinks before designing a computer system incorporating them.

What is desired, therefore, is to provide a measuring apparatus which can conveniently measure thermal resistance of a heat sink.

SUMMARY OF THE INVENTION

An exemplary thermal resistance measuring apparatus for a heat sink includes a heat source, a temperature sensor, a micro control unit (MCU), a display, and a power apparatus. The heat source heats the heat sink. The temperature sensor senses temperature of the heat source. The MCU receives temperature signals from the temperature sensor and processes them to calculate thermal resistance of the heat sink. The display is electrically connected to the MCU for showing the thermal resistance of the heat sink. The power apparatus supplies power to the heat source, the temperature sensor, and the MCU.

Other advantages and novel features will become more apparent from the following detailed description when taken in conjunction with the accompanying drawings, in which:

DETAILED DESCRIPTION OF THE INVENTION

Figure 1:
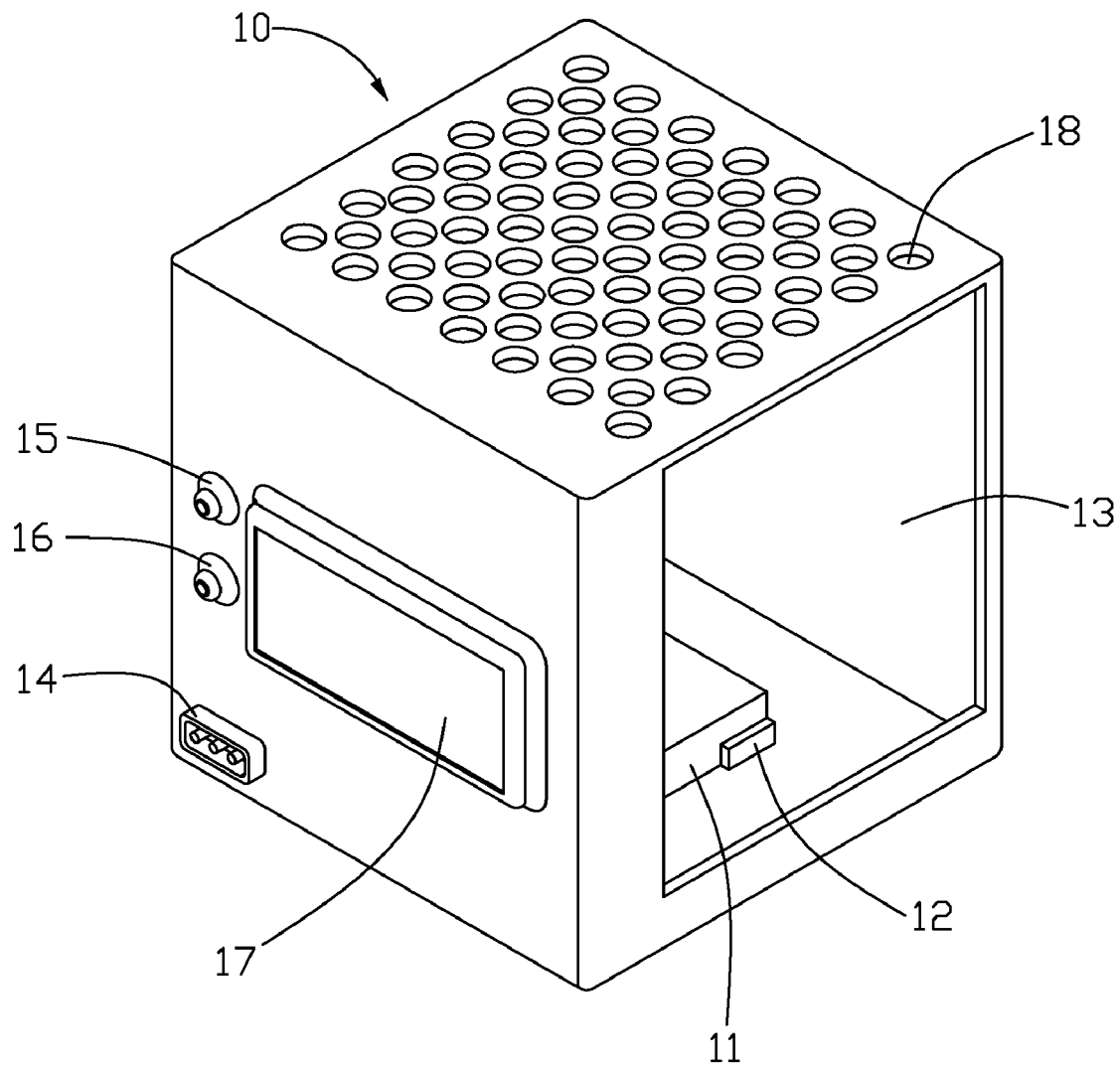
FIG. 1 is an isometric view of a thermal resistance measuring apparatus in accordance with a preferred embodiment of the present invention.
Figure 2:
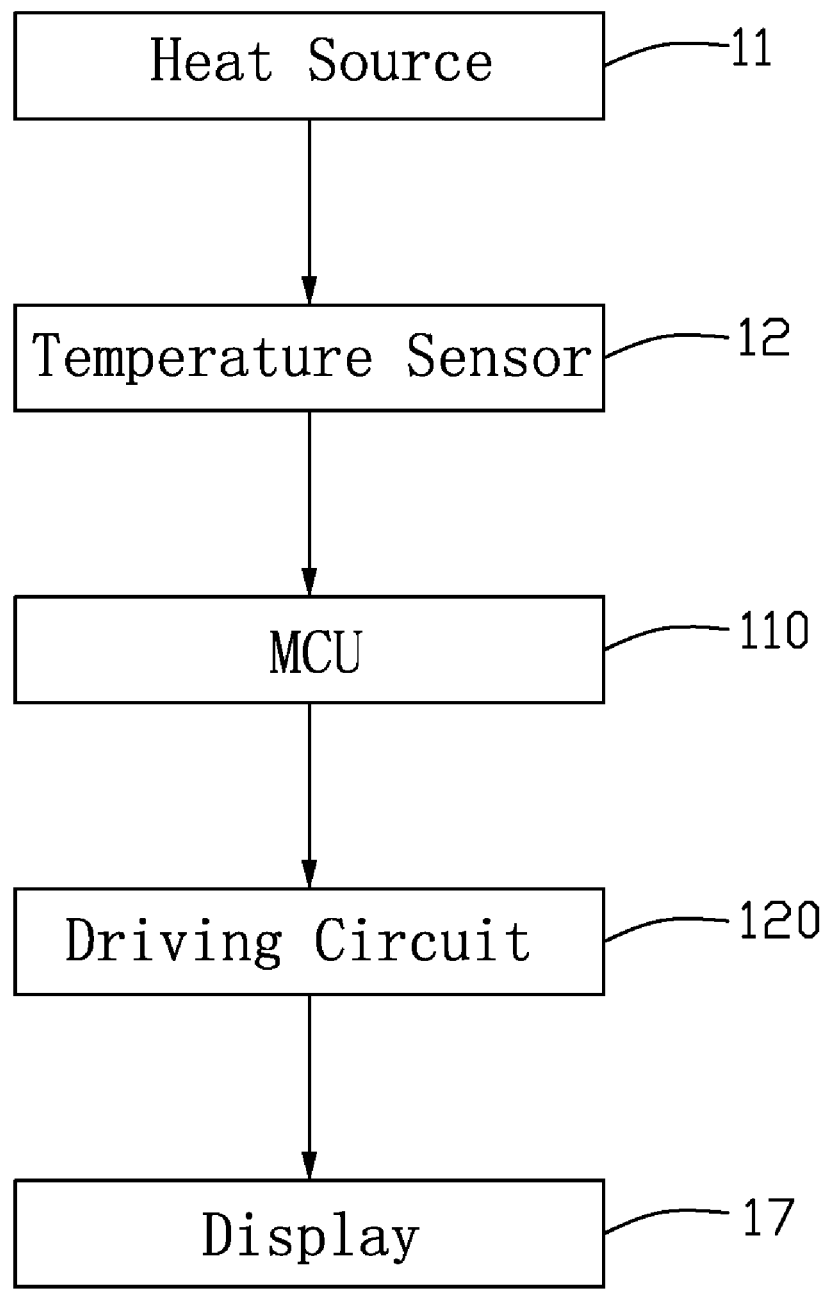
FIG. 2 is a block diagram of FIG. 1.

Referring to FIGS. 1 and 2, a thermal resistance measuring apparatus in accordance with a preferred embodiment of the present invention is shown. The measuring apparatus includes a cubic-shaped case 10. The case 10 is typically hollow, and a heat source 11, a temperature sensor 12, and a circuit board (not shown) are installed on a bottom of the case 10. The circuit board includes a micro control unit (MCU) 110 and a driving circuit 120. One side of the case 10 has a hatch 13. Another side of the case 10 has a power apparatus such as a power connector 14, a power button 15, a reset button 16, and a display 17 thereon. A top side of the case 10 defines a plurality of through holes 18 therein for dissipation of heat.

In this embodiment, the heat source 11 is an aluminum oxide ceramic heating plate. The temperature sensor 12 is a programmable resolution 1-wire digital thermometer. The display 17 is a liquid crystal display (LCD).

The heat source 11 is electrically connected to an input terminal of the MCU 110 via the temperature sensor 12. An output terminal of the MCU 110 is electrically connected to the display 17 via the driving circuit 120. The power connector 14 is connected to a power pin of the heat source 11, a power pin of the temperature sensor 12, and a power pin of the driving circuit 120 via the power button 15 for supplying power. The power connector 14 is also connected to a power pin of the MCU 110 via the power button 15. The reset button 16 is connected to a reset pin of the MCU 110. According to a thermal resistance formula, a corresponding program of the MCU is set therein. The thermal resistance formula is:

$$TR=(Tm-Te)/Pw$$

Where TR is the thermal resistance of a heat sink 20 (FIG. 3) mounted on the top surface of the heat source 11, Tm is the maximum temperature of a top surface of the heat source 11 when it works under the rated power thereof, Te is room temperature, and Pw is the rated power of the heat source 11 (Pw is usually supplied by the product specification of the heat source 11).

Figure 3:
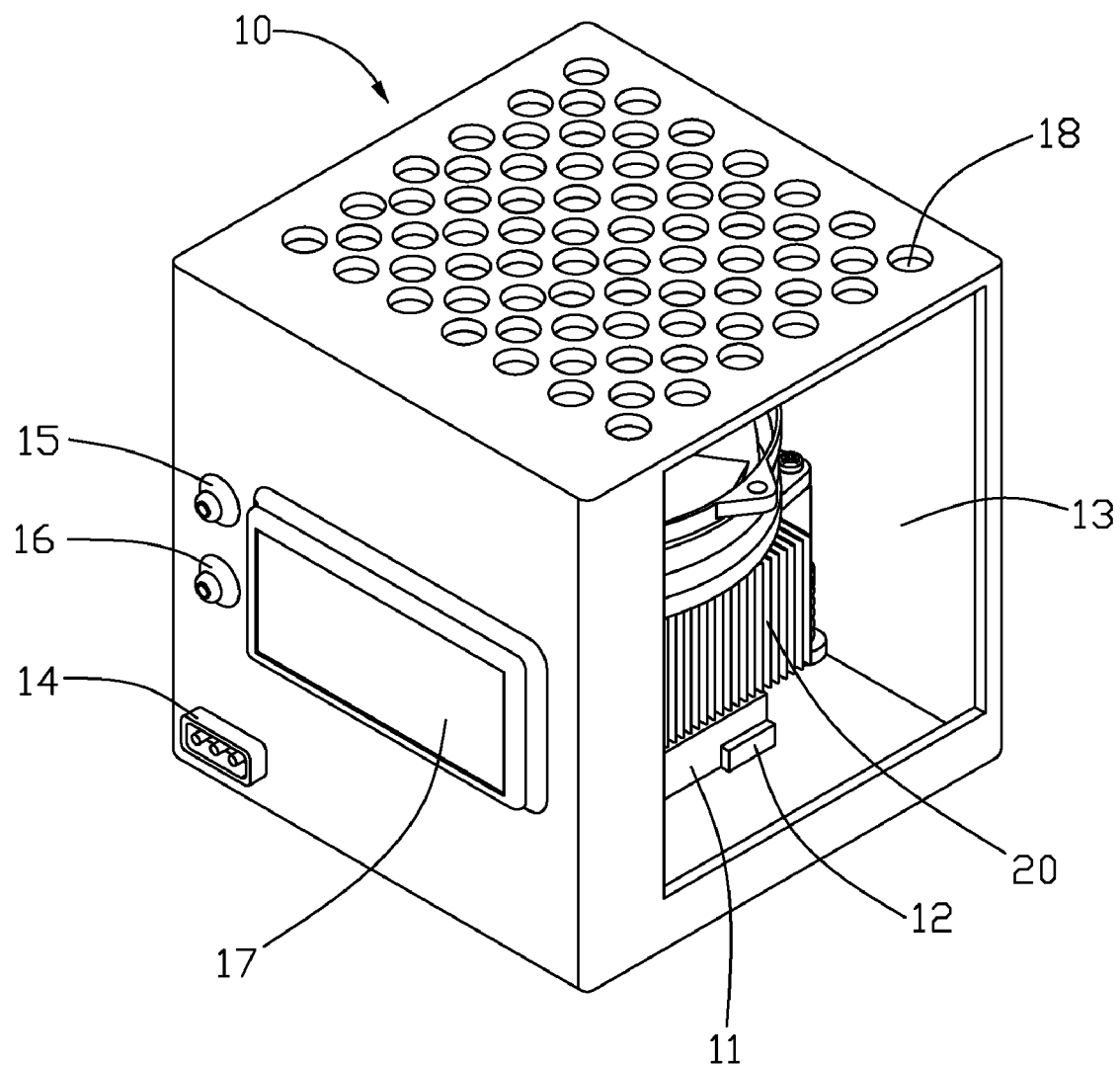
FIG. 3 is an isometric view of the thermal resistance measuring apparatus of FIG. 1, with a heat sink attached thereinto.

Referring also to FIG. 3, the heat sink 20 is put into the case 10 and attached to the top surface of the heat source 11. A power connector of the heat sink 20 and the power connecter 14 are connected to an external power source (not shown). After pressing the power button 15, the heat source 11 reaches the heated temperature Tm. The temperature sensor 12 senses temperature of the heat source 11, and transmits them to the MCU 110 (the room temperature Te is an initial temperature of the heat source 11). The MCU 110 processes data of the temperature signals and calculates the thermal resistance TR of the heat sink 20 according to the aforesaid thermal resistance formula, and then the MCU 110 controls the driving circuit 120 to output the data of the thermal resistance TR via the display 17. Thereby, designers can conveniently measure thermal resistances of heat sinks in actual working conditions, and use the data to design an optimal heat dissipation system.

If the MCU 110 can drive the display 17, the driving circuit 120 can be deleted. The MCU 110 can be directly electrically connected to the display 17. The power connector 14 can also be replaced by an internal power source arranged in the case 10 according to need.

It is to be understood, however, that even though numerous characteristics and advantages of the preferred embodiments have been set forth in the foregoing description, together with details of the structures and functions of the embodiments, the disclosure is illustrative only, and changes may be made in detail, especially in matters of shape, size, equivalent material and arrangement of parts within the principles of the invention to the full extent indicated by the broad general meaning of the terms in which the appended claims are expressed.

What is claimed is:

1. A thermal resistance measuring apparatus for a heat sink, comprising:

a heat source configured for heating the heat sink;

a temperature sensor configured for sensing temperature signals of the heat source;

micro control unit (MCU) configured for receiving the temperature signals from the temperature sensor and processing them to calculate thermal resistance of the heat sink;

a display electrically connected to the MCU for showing the thermal resistance of the heat sink; and a power apparatus for supplying power to the heat source, the temperature sensor, and the MCU, wherein the MCU calculates the thermal resistance of the heat sink by the following formula:

$$TR=(Tm-Te)/Pw$$

where TR is the thermal resistance of the heat sink, Tm is the maximum temperature of the heat source when the heat source works under the rated power thereof, Te is room temperature, and Pw is the rated power of the heat source.

2. The thermal resistance measuring apparatus as claimed in claim 1, further comprising:

a case, wherein the heat source, the temperature sensor, and the MCU are arranged in the case, and the display is installed on one side of the case.

3. The thermal resistance measuring apparatus as claimed in claim 2, wherein a power button and a reset button are arranged on the case, the power apparatus is connected to a power pin of the MCU via the power button, the reset button is connected to a reset pin of the MCU.

4. The thermal resistance measuring apparatus as claimed in claim 2, wherein a plurality of through holes is defined in a top side of the case.

5. The thermal resistance measuring apparatus as claimed in claim 2, wherein the power apparatus is a power connector installed on the case configured for electrically connecting an external power source.

6. The thermal resistance measuring apparatus as claimed in claim 2, wherein the power apparatus is an internal power source installed in the case.

7. The thermal resistance measuring apparatus as claimed in claim 1, wherein the heat source is an aluminum oxide ceramic heating plate.

8. The thermal resistance measuring apparatus as claimed in claim 1, wherein the temperature sensor is a programmable resolution 1-wire digital thermometer and contacts the heat source.

9. The thermal resistance measuring apparatus as claimed in claim 1, wherein the display is a liquid crystal display (LCD).

10. A thermal resistance measuring apparatus comprising:

a case;

a heat source received in the case, and configured for being supplied with power to reach a desired temperature which depends on the related power of the heat source, a heat sink attached to a surface of the heat source;

a temperature sensor contacting the heat source for sensing temperature signals thereof;

a micro control unit (MCU) connected to the temperature sensor for receiving the temperature signals and processing them to calculate thermal resistance of the heat sink;

a display electrically connected to the MCU for showing the thermal resistance of the heat sink; and a power apparatus connected to the display, the temperature sensor, and the MCU for supplying power thereto, where the MCU calculates the thermal resistance of the heat sink by the following formula:

$$TR=(Tm-Te)/Pw$$

where TR is the thermal resistance the heat sink, Tm is the maximum temperature of the heat source when the heat source works under the rated power thereof, Te is room temperature, and Pw is the rated power of the heat source.

11. The thermal resistance measuring apparatus as claimed in claim 10, further comprising a driving circuit electrically connected between the MCU and the display for driving the display.

12. The thermal resistance measuring apparatus as claimed in claim 10, wherein the heat source is an aluminum oxide ceramic heating plate.

13. The thermal resistance measuring apparatus as claimed in claim 10, wherein the temperature sensor is a programmable resolution 1-wire digital thermometer.

14. The thermal resistance measuring apparatus as claimed in claim 10, wherein the display is a liquid crystal display (LCD).

* * * * *